(12) United States Patent
Davis et al.

(10) Patent No.: US 11,725,220 B1
(45) Date of Patent: Aug. 15, 2023

(54) PRODUCTION OF FUSEL LACTATES VIA BIOCATALYSIS

(71) Applicants: National Technology & Engineering Solutions of Sandia, LLC, Albuquerque, NM (US); Arizona Board of Regents on behalf of Arizona State University, Phoenix, AZ (US)

(72) Inventors: Ryan Wesley Davis, San Jose, CA (US); Arul Mohzy Varman, Tempe, AZ (US); Aditya Pandharinath Sarnaik, Tempe, AZ (US); Amit Kumar Jha, Livermore, CA (US)

(73) Assignees: National Technology & Engineering Solutions of Sandia, LLC, Albuquerque, NM (US); Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 17/003,061

(22) Filed: Aug. 26, 2020

(51) Int. Cl.
  *C12N 1/20* (2006.01)
  *C12P 7/62* (2022.01)

(52) U.S. Cl.
  CPC . *C12P 7/62* (2013.01); *C12N 1/20* (2013.01)

(58) Field of Classification Search
  None
  See application file for complete search history.

(56) References Cited

U.S. PATENT DOCUMENTS

| 9,732,363 | B2 * | 8/2017 | Tsuchida | C12P 7/10 |
| 2006/0035353 | A1 * | 2/2006 | Zhao | C12P 7/06 |
| | | | | 435/189 |
| 2013/0197248 | A1 | 8/2013 | Nielsen et al. | |
| 2015/0140620 | A1 * | 5/2015 | Zhang | C12P 7/62 |
| | | | | 435/254.11 |

FOREIGN PATENT DOCUMENTS

| CN | 1594585 A | 3/2005 |
| CN | 102164986 B | 12/2013 |
| WO | 2012017083 A1 | 2/2012 |

OTHER PUBLICATIONS

Tai, et al., "Engineered Biosynthesis of Medium-Chain Esters in *Escherichia coli*", In Metabolic Engineering, vol. 27, 2015, pp. 20-28.
Lee, et al., "Microbial Biosynthesis of Lactate Esters", In Biotechnology for Biofuels, vol. 12, No. 226, 2019, 20 pages.
Ecopha Group, "Bio-Ethanol Ethyl Lactate", Retrieved At: <<https://ecopha.com/our-innovation/>>, Retrieved Date: Aug. 18, 2020, 7 pages.
Delgado, et al., "Ethyl Lactate Production Via Esterification of Lactic Acid With Ethanol Combined With Pervaporation", In Chemical Engineering Journal, vol. 165, 2010, pp. 693-700.
Jarboe, et al., "Metabolic Engineering for Production of Biorenewable Fuels and Chemicals: Contributions of Synthetic Biology", In Journal of Biomedicine and Biotechnology, vol. 2010, Article ID 761042, 2010, 18 pages.
Robinson, Peter K., "Enzymes: Principles and Biotechnological Applications", In Essays in Biochemistry, vol. 59, 2015, pp. 1-41.
Peng, et al., "Accurately Determining Esterase Activity Via the Isosbestic Point of p-Nitrophenol", In BioResources, vol. 11, No. 4, 2016, pp. 10099-10111.
Pereira, et al., "A Novel Process for the Ethyl Lactate Synthesis in a Simulated Moving Bed Reactor (SMBR)", In Chemical Engineering Science, vol. 64, 2009, pp. 3301-3310.
Holland, et al., "Esterases of Lactic Acid Bacteria and Cheese Flavour: Milk Fat Hydrolysis, Alcoholysis, and Esterification", In International Diary Journal, vol. 15, 2005, pp. 711-718.
Pereira, et al., "Ethyl Lactate as a Solvent: Properties, Applications, and Production Processes—A Review", In Green Chemistry, vol. 13, 2011, pp. 2658-2671.

* cited by examiner

*Primary Examiner* — Tekchand Saidha
(74) *Attorney, Agent, or Firm* — Madelynne J. Farber; Samantha Updegraff; Eschweiler & Potashnik, LLC

(57) ABSTRACT

Microbial enzymes are used for esterification of biomass-derived substrates for production of industrially valuable esters. *E. coli* was used as an efficient platform for recombinant synthesis of fusel lactates such as the green solvent ethyl lactate.

20 Claims, 12 Drawing Sheets

PRODUCTION OF FUSEL LACTATES VIA BIOCATALYSIS

STATEMENT OF GOVERNMENTAL INTEREST

This invention was made with Government support under Contract No. DE-NA0003525 awarded by the United States Department of Energy/National Nuclear Security Administration. The Government has certain rights in the invention.

FIELD

This disclosure relates to biomass constituent conversion into valuable products. More specifically, this disclosure relates to biochemical pathways for biomass valorization.

BACKGROUND

With the advent of environmental safety policies and development of sustainable industrialization practices, global efforts are being made towards the use of biodegradable organic solvents like lactate esters. Esters have been commercially used as solvents, in lubricants, fuel additives, food and pharmaceutical industries, etc. Owing to their ever-increasing global demand, efforts are being made world-wide for their economical production.

Ester solvents are typically made through petrochemical processes, but the chemical esterification process for its production is thermodynamically and environmentally unfavourable. The synthesis of these materials through biocatalysis; either using genetically modified microbial cell factories or in vitro reactions would be desirable alternative. Biological production of industrially valuable chemicals from renewable sources also imparts sustainability to the process of manufacturing.

Lactate esters, such as ethyl lactate, are useful chemical compounds. Ethyl lactate is biodegradable, nontoxic, and easy to recycle. It is used in fragrances, pharmaceutical industry, and food additives. In addition to these properties, it has been found to meet or exceed the efficacy of traditional organic solvents like toluene, methyl ethyl ketone, and N-methyl-pyrrolidone in many applications. This makes ethyl lactate a primary focus for industrial attention.

Currently, the organic chemistry-based process used for the synthesis of ethyl lactate is energy intensive, expensive, and potentially detrimental to the environment. A renewable source and process for making this material would meet a long-felt need and be a welcome development.

SUMMARY

Disclosed herein is an introduction and overexpression of a combination of genes for enzymatic production of fusel lactates from biomass in a strain of *E. coli* that produces ethanol. The term "fusel lactate" is meant to encompass a lactate with a $C_2$ to $C_5$ ester group, such as, for example, ethyl, isopentyl, isopropyl, (iso)butyl, and (iso)pentyl lactate.

Enzyme catalysis is one of the ways to synthesize fusel lactates with lower energy input than prior art methods and improved specificity. Cloning these enzymes in microbes through genetic engineering and metabolic manipulations would leverage the organism's capacity for bioproduction, taking important steps towards sustainable development.

The enzymes include lactate synthase and various esterases. In particular, heterologous genes were cloned from different organisms in *E. coli* for diverting its central metabolic pathway (predominantly involved in energy and biomass generation) towards ethyl lactate synthesis. Disclosed herein are in vivo (genetic engineering of microbes like *E. coli*) and in vitro enzyme catalysis for the production of green or biodegradable fusel lactates like ethyl lactate. The engineered fermentation strain was confirmed to produce ethyl lactate by GC-MS using minimal medium. Ethyl lactate is a renewable solvent that has been identified as a priority target for biobased chemicals. Owing to faster growth, minimal nutritional requirement of the organism, and extracellular release of ethyl lactate, a continuous fermentation and product extraction process as disclosed herein could be successfully implemented for industrial scale-up using the strains disclosed herein.

In an embodiment, a process for converting a glucose-containing hydrolyzed biomass into a fusel lactate, includes the steps of: expressing an acyl-alcohol transferase gene, esterase gene, or both in a bacterial host, the bacterial host being added to or already present in the glucose-containing hydrolyzed biomass; maintaining conditions suitable for fermenting in the hydrolyzed biomass, the fermenting producing an alcohol and a lactate; and catalyzing through an enzyme encoded by the acyl-alcohol transferase gene or esterase gene, a reaction from the alcohol and lactate to form a fusel lactate in the bacterial host.

In an embodiment, an engineered fermentation strain includes: an *E. coli* host, and the *E. coli* host includes an expression of an enzyme selected from the group consisting of: acyl-coenzyme A, ethyl-ester-synthase-1, diacylglycerol-transferase, ethanol-o-acyltransferase, acetylxylan-esterase-2, carbohydrate-esterase, esterase-A, truncated-esterase-A, or combinations thereof.

The term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something and is not intended to indicate a preference.

"Consisting essentially of" in this instance, means the specified material and others that do not materially affect the basic and novel characteristics of the methods, articles of manufacture, or compositions listed herein. For example, an unspecified material that does not materially affect the basic and novel characteristics of the methods, articles of manufacture, or compositions listed herein, in an amount of less than about 5%, less than about 3%, or less than about 1% may be encompassed by this term.

DETAILED DESCRIPTION

Figure 1:
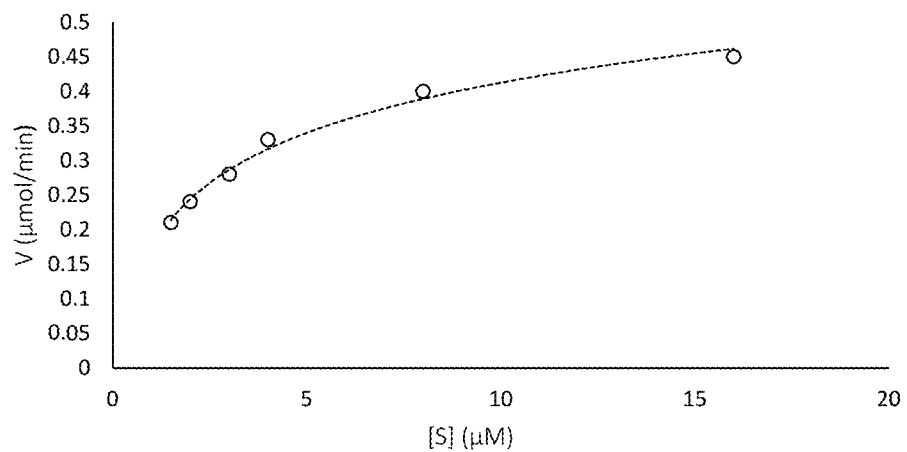
FIG. 1 is an example of a Michaelis-Menten plot.

Disclosed herein is an enzymatic process for esterification of hydrolyzed biomass through a microbial route. It is based on biocatalysis for condensation of organic acids or Coenzyme A (CoA) adducts thereof with alcohols. Microbial systems capable of producing both substrates and enzymes can catalyze the biosynthesis of hydrolyzed biomass to produce industrially valuable lactate esters at ambient temperatures.

Also disclosed herein is a bioprospecting process for partially annotated enzymes, esterases (using organic acids as substrates), or acyl-alcohol transferases (using CoA adducts of organic acids as substrates) and cloning these into microbial host systems (generically referred to herein as enzymes), for in vitro or in vivo catalysis of the biosynthetic materials.

In an embodiment, this encompasses metabolic engineering of *Escherichia coli* for production of ethyl lactate through heterologous expression of acyl-alcohol transferase and Esterase genes. *Saccharomyces cerevisiae, Pseudomonas aeruginosa* and *Brettanomyces bruxellensis* AWRI1499 were selected to mine for the enzymes.

Disclosed herein is a three part substantiation process; (1) in vitro analysis to discover enzyme sequences and corrections (if non-annotated); (2) cloning these sequences along with organic acid (for e.g. lactate dehydrogenases) and alcohol (for e.g. alcohol dehydrogenases) producing genes; and (3) in vivo metabolic modulations for recombinant synthesis of fusel lactate.

An advantage of using biomass energy and material sources as starting materials are that they are renewable resources. Sources of biomass include dedicated energy crops, such as herbaceous or woody crops; crop residues, such as stalks and leaves of agricultural crops; forestry residues, such as unmerchantable timber remnants; and even algal or cyanobacterial feedstocks. Other sources include wood processing residues, such as sawdust; municipal waste, such as sorted recyclable materials; or wet waste, such as sewage. Of particular interest and suitability for the process disclosed herein are cellulosic, glucose-containing biomass, such as woody or herbaceous biomass.

Conversion of hydrolysates in the biomass using biological catalysts is accomplished herein by use of a bacteria that produces enzymes for bioconversion. Bacteria include, e.g., *Saccharomyces, E. coli, Lactobacillus, Clostridium,* and a host of others). This generates a variety of common high-yielding intermediates from various acidogenic and solvetogenic biochemical pathways in homo- or heterofermentative processes. See Chapter 11: Fermentation Pathways, Microbial Physiology. Albert G. Moat, John W. Foster and Michael P. Spector (2002). ISBN: 0-471-39483-1, incorporated herein by reference. Furthermore, recent advances in synthetic biology and metabolic engineering significantly expand the ability to generate a host of biochemical intermediates with substantially improved bioconversion rates, yields, and titers. See Choi, et al, "Systems Metabolic Engineering Strategies: Integrating Systems and Synthetic Biology with Metabolic Engineering," Trends in Biol. Vol. 37, 8, p. 817-837, Aug. 1, 2019, incorporated herein by reference.

Among the biochemical compounds within 1-2 enzymatic steps from central metabolism are a variety of short-chain ($C_2$-05) hydroxyalkanoates, such as: alpha-hydroxy-acids, including lactate, glycolate, alpha-hydroxy butyrate, and alpha-hydroxy valerate; gamma-hydroxy acids, including 3-hydroxy-propionate, and 4-hydroxy-butyratre; and various short-chain ($C_2$-05) alcohols, including ethanol, (iso) propanol, (iso)butanol, and (iso)pentanols, commonly denoted as 'fusel' alcohols. See Noor, et al, "Central Carbon Metabolism as a Minimal Biochemical Walk between Precursors for Biomass and Energy," Molecular Cell Vol. 39 Iss. 5, p. 809-820 (Sep. 10, 2010), incorporated herein by reference.

In an embodiment, a cellulosic biomass is hydrolyzed; for example, with a dilute or weak acid. This converts the glucose-containing biomass to a suitable substrate for fermentation. In an embodiment, the hydrolysate should be pH adjusted from about 0 to about 5.2 for fermentation, such as 2 to 5, or 3 to 4.5. Hydrolyzed biomass can be purchased or made by published methods. An example glucose-containing hydrolyzed biomass is DMR hydrolysate from deacetylated corn stover biomass. This contains monomers of glucose and lactate, among other things, and is suitable for a monomeric substrate for fermentation.

The process disclosed herein can be applied to racemic or enantiomer selected mixtures of the lactate monomer from hydrolyzed glucose-containing biomass. In an embodiment, an enantiomeric selection of the lactate monomers in the biomass can be made. Amongst the enantiomers of lactate, D-lactate is favored for material formation, such as polymers. D-lactate is the primary precursor of Poly-D-lactic acid. Poly-D-lactic acid is a bio-based polymer that is an economically feasible packaging material. It is also favored for making solvents. The D enantiomer is less common and more difficult to separate.

In a racemic mixture, the L enantiomer is dominant. For biofuel applications, a racemic mixture is suitable for further processing.

Ethyl lactate can be produced directly from lactic acid and ethanol through a heterogeneously catalyzed esterification reaction, as seen in Reaction (I):

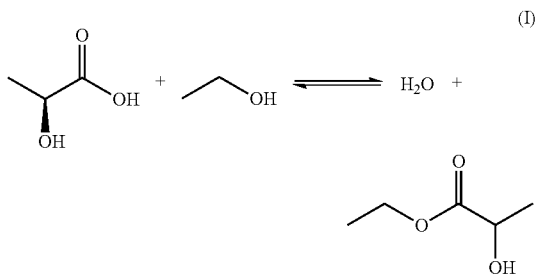

Microorganisms present in biomass naturally produce lactic acid and ethanol and can be engineered to increase production of those metabolites. Though enzymes catalyzing an esterification reaction between lactic acid and ethanol do not change the thermodynamics of the reaction, they do allow the reaction to proceed at a faster rate.

In addition, due to the complex metabolism of microorganisms, it is possible to change the route by which ethyl lactate is produced. Rather than combining ethanol and lactic acid by esterification through use of an esterase, ethanol can be combined with lactyl-CoA by means of condensation through use of an alcohol acyltransferase (AAT). See Reaction (II).

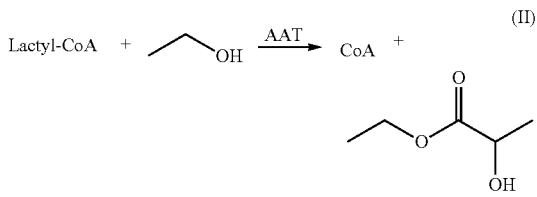

Accordingly, in an embodiment, microorganisms can be engineered to produce ethyl lactate from biomass by either: reacting ethanol and lactic acid metabolites through an esterase or reacting ethanol and Lactyl-CoA metabolites through an alcohol acyltransferase.

A gene mining in vitro process was performed to identify enzymes that would be most effective for converting hydrolyzed biomass into fusel lactates. Enzymes were selected from Brettanomyces, which is known to synthesize esters during wine fermentation. On the basis of sequence homology with fatty acyl-alcohol transferase that catalyses esterification of fatty acids with alcohols, four enzymes from Brettanomyces, diacylglycerol acyltransferase, ethanol-o-acyltransferase, acetyl-xylan esterase, and carbohydrate esterase family-9 were identified using blastp analysis.

The polynucleotide and polypeptide sequences for these genes was not accomplished in the Genbank or Uniprot databases. The sequences were manually compared, and genes were designed through sequence homology with other genes in the database amino acid polarity and structural similarity. It is believed that the Brettanomyces genes synthesized through this process do not exhibit naturally.

On the basis of previous literature, esterases and transferases were selected from Saccharomyces and Pseudomonas. The sequences were codon optimized and synthesized from Twist Biosciences. Genes were cloned for lactate dehydrogenase (for both D- as well as L-lactic acid). Esterases use lactate as their substrates while transferases require 'lactyl Co-A' as the substrate. To obtain 'lactyl Co-A' from lactic acid and acetyl Co-A (product of central metabolism), propionyl Co-A transferase gene from Clostridium propionicum was cloned along with other genes.

It was found that a mixture of esterases and alcohol acyltransferases: AcAlt, EEB1, DAG, EOA, AXE2, CE, EstA, and tEstA had good potential to esterify glucose-containing hydrolyzed biomass to produce fusel lactates. See Table 1. These enzymes were further investigated for further use in the fusel lactate biosynthesis. It should be understood that the gene encodes the enzyme with the similar name for biological transcription.

TABLE 1

| Gene | Enzyme Name | Species of Origin | Type |
|---|---|---|---|
| PET (control) | — | Escherichia coli | WT |
| AcAlt | Acyl-coenzyme A | Komagataella phaffii | AAT |
| EEB1 | Ethyl-ester-synthase-1 | Saccharomyces cerevisiae | Esterase |
| DAG | Diacylglycerol-transferase | Brettanomyces bruxellensis | AAT |
| EOA | Ethanol-o-acyltransferase | Brettanomyces bruxellensis | AAT |
| AXE2 | Acetylxylan-esterase-2 | Brettanomyces bruxellensis | Esterase |
| CE | Carbohydrate-esterase | Brettanomyces bruxellensis | Esterase |
| EstA | Esterase-A | Pseudomonas aeruginosa | Esterase |
| t-EstA | Truncated-esterase-A | Pseudomonas aeruginosa | Esterase |

PET is a control strain of E. coli (BL21) with only an empty plasmid, and tEstA is a truncated form of the EstA gene. Each of the genes has previously been cloned into BL21 E. coli, which is the host organism used to produce enzymes disclosed in the Examples. As alcohol acyltransferases and esterases, all of the enzymes listed in Table 1 were selected for the potential to facilitate the synthesis of fusel lactates from glucose-containing hydrolyzed biomass.

In an embodiment, a combination of one or more of the species in Table 1 can be utilized in the process disclosed herein. In an embodiment, the acyl-alcohol transferase gene or esterase gene are derived from Komagataella phaffii, Saccharomyces cerevisiae, Brettanomyces bruxellensis, or Pseudomonas aeruginosa and the enzyme is non-naturally occurring.

The selected enzymes were further tested to determine whether they have the functionality to synthesize ethyl lactate. In order to measure the esterase functionality, in-vitro reaction assay can be performed using pNPA as a substrate.

Esterase activity is used to indirectly measure the esterification activity required for enzymes to produce ethyl lactate. Cleavage of the ester bond in 4-nitrophenyl acetate (pNPA) to form 4-nitrophenol (pNP) and acetic acid is used to determine the esterase activity of the enzymes. The Km and Vmax values, found by applying the Michaelis-Menten kinetics model to experimental data found at optimal pH and temperature conditions, are used to evaluate enzymatic activity. As disclosed herein, hydrolysis of the ester bond in pNPA was used to estimate the esterification activity of the enzymes.

Esterification activity can be measured through the pNPA cleavage. Though esterase enzymes are capable of targeting and cleaving ester bonds, they are also known to exhibit esterification activity. Because of this dual activity of esterases, it is possible to indirectly measure their esterification activity through measuring their esterase activity—for example, through the use of pNPA. The reaction of 4-nitrophenyl acetate (pNPA) to form 4-nitrophenol (pNP) and acetic acid involves the cleavage of an ester bond, as shown in Reaction (III):

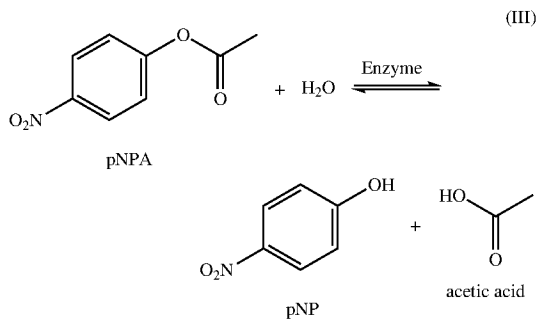

(III)

The benefit of using pNPA to measure esterase activity is that the product pNP has a yellow color in the presence of NaOH. The absorbance of pNP can therefore be measured (at 410 nm), and the progress of the reaction can be measured in real time. For these reasons, pNPA reaction assays can be used for enzymatic activity optimization and for estimation of kinetic parameters.

Two parameters that can influence the function of enzymes, and therefore be optimized for kinetic activity, are temperature and pH. By allowing the pNPA conversion to pNP reaction to proceed at different temperatures and pHs for a specific amount of time, the extent of reaction can be determined. The best conditions are those that result in the highest extent of reaction, or product concentration.

Enzymatic activity can be characterized by calculating kinetic parameters for the enzymes considered. To calculate kinetic parameters for an enzyme, a kinetic model must be applied to the data. For example, the Michaelis-Menten model has been found to adequately model activity for a wide selection of enzymes. The Michaelis-Menten equation is as seen in Equation 1:

$$v = \frac{v_{max}[S]}{k_m + [S]} \quad [1]$$

In the Michaelis-Menten equation, v represents the reaction rate, and [S] represents substrate concentration. FIG. 1 represents a typical Michaelis-Menten plot.

The kinetic parameters for the enzyme are $v_{max}$ and $k_m$. These parameters represent the maximum reaction rate and the Michaelis-Menten constant, respectively. For a given enzyme, the $k_m$ value represents the substrate concentration at which the reaction rate is one half of the maximum possible reaction rate for that enzyme. The larger the $v_{max}$ value, the faster the potential reaction rate when catalyzed by the enzyme. The smaller the $k_m$ value ($k_m < 1 \times 10^{-4}$), the less substrate is required for the catalysis reaction to approach the maximum reaction rate. In an embodiment, the $v_{max}$ and $k_m$ of the enzymes disclosed herein are improved over a PET control. For example, the $v_{max}$ may exceed $1.5 \times 10^{-6}$ mol/(L*s), such as $1.6 \times 10^{-6}$ to $2 \times 10^{-6}$, or $1.7 \times 10^{-6}$ to $1.9 \times 10^{-6}$ mol/(L*s). Also, or separately, the $k_m$ may be less than $30.2 \times 10^{-6}$M, such as 21 to $1 \times 10^{-6}$M, or 18 to $3 \times 10^{-6}$M.

Another useful parameter for characterizing enzymes is known as the turnover number, $k_{cat}$. The equation for determining $k_{cat}$ is Equation 2:

$$k_{cat} = \frac{v_{max}}{[E_T]} \quad [2]$$

The turnover number is the ratio of the maximum reaction rate and the number of enzymes present. This value essentially states how much substrate is converted to product per enzyme in a given unit of time—assuming the enzyme is saturated by the substrate.

A further parameter of interest is the ratio of $k_{cat}$ to $k_m$. This ratio is known as the specificity constant, and has a diffusion limited maximum value of around $10^9$ $M^{-1}s^{-1}$. An enzyme which approaches that diffusion limited value is said to have reached catalytic perfection. The specificity constant is a useful tool for comparing enzymes with higher values representing higher catalytic efficiencies.

With the goal of determining kinetic parameters for enzymes, analysis of kinetic data for an enzymatic reaction involves linearizing the Michaelis-Menten model, as seen in Equation 3:

$$\frac{1}{v_0} = \frac{k_m}{v_{max}}[S_0] + \frac{1}{v_{max}} \quad [3]$$

Figure 2:
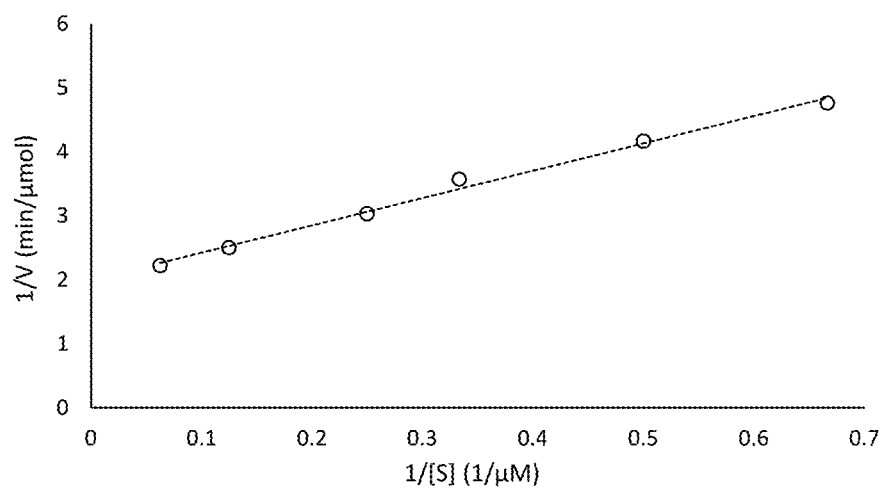
FIG. 2 is an example of a Lineweaver-Burke plot.

In this form, only the initial reaction rate and substrate concentrations are considered—with the initial reaction rate being the average change in product concentration between the reaction initiation and the first subsequent reading. Plotting the inverse of $v_0$ against the inverse of $[S_0]$ results in what is known as a Lineweaver-Burk plot. An example of a Lineweaver-Burk plot is seen in FIG. 2.

A linear regression of the data in such plots follows the linearized Michaelis-Menten equations. The y-intercept of the Lineweaver-Burk plot is the inverse of $v_{max}$; the slope multiplied by $v_{max}$ gives the value of the $k_m$ parameter. This is summarized in Equation 4:

$$v_{max} = \frac{1}{b}; k_m = mv_{max} \quad [4]$$

Therefore, the kinetic parameters of an enzyme can be determined through the parameters obtained through a linear regression applied to linearized kinetics data. Once $v_{max}$ and $k_m$ are determined, they can be used to calculate the turnover number and the specificity constant. This approach utilizes experiments being performed with varying initial substrate concentrations while holding all other parameters constant.

Once the specificity constant is calculated, it is possible to determine which of the enzymes performed best in catalyzing esterase activity. Because esterase activity is suggestive of esterification activity, it can be assumed that the enzyme with the best esterase activity will have the highest specificity constant for fusel lactate production.

In vitro experiments were performed to determine the optimal temperature and pH conditions for enzymatic activity, and to collect enzyme reaction kinetics data. The Michaelis-Menten model was applied the kinetic data and $v_{max}$, $k_m$, $k_{cat}$, and specificity constant values were calculated. AXE2 had the lowest $k_m$ value at $1.2 \times 10^{-6}$ M. AcAlt had the highest $v_{max}$, $k_{cat}$, and specificity constant values at $1.89 \times 10^{-6}$ Ms$^{-1}$, 2.31 s$^{-1}$, and $3.59 \times 10^5$ M$^{-1}$s$^{-1}$, respectively.

All enzymes had the higher specificity constant values than the control, suggesting that all enzymes have potential for ethyl lactate production. DAG and EOA were found to not have the promiscuity necessary to catalyze the hydrolysis of the ester bond in pNPA, but still have potential for ethyl lactate production. Based on the results of this experiment, it is expected that AcAlt, EEB1, and CE would have the best catalytic efficiency for the production of ethyl lactate.

In an embodiment, in vivo reactions (i.e., in the fermentation strain in a reaction vat including the biomass materials) can be conducted with the identified enzymes, without separating out just the reactants from the biomass. The enzymes can be heterologously expressed in a bacterial host (*E. coli*) and added to the fermentation strain to provide a biocatalyst as a living, growing system. In an embodiment, *Corynebacterium glutamicum* can also be used as the host. The bacterial host functions as self-replicating sources of enzymes and DNA material. It feeds on glucose material in the biomass, using it as an energy source, replicates the expressed enzymes that will catalyze the intended reaction by way of organic acids, Coenzyme A (CoA) adducts thereof, and alcohols present in the glucose-containing biomass into fusel lactates such as ethyl lactate.

Figure 3:
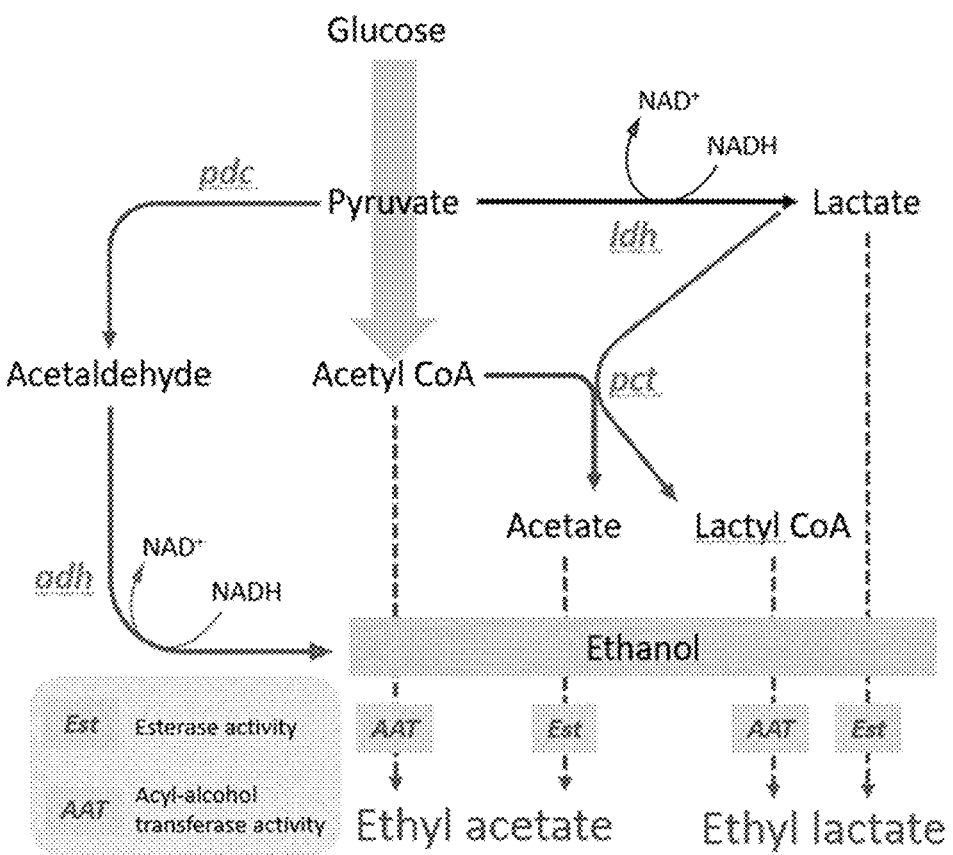
FIG. 3 is an example metabolic pathway of the in vivo process contemplated herein including the esterase and acyl-alcohol transferase activity.

FIG. 3 shows a summary metabolic pathway indicating an embodiment of the in vivo process contemplated herein. The cells are engineered to synthesize substantial amount of lactate (by cloning D/L lactate dehydrogenase enzyme) from pyruvate and alcohol (for example, ethanol by cloning pyruvate decarboxylase (pdc) and alcohol dehydrogenase (adh) enzymes) in the cell.

As shown in FIG. 3, esterase enzymes (exhibiting 'Est'), such as those shown in Table 1 can effectively convert these substrates into corresponding esters, however acyl-alcohol transferases (such as those shown in Table 1) (exhibiting 'AAT') utilize CoA-adduct organic acid substrates (like acetyl CoA) for ester synthesis. Therefore, one more enzyme 'propionate CoA transferase' (pct) was cloned, which can convert lactate to lactyl CoA, and this can be further utilized through AAT activity for ethyl lactate synthesis.

Figure 4:
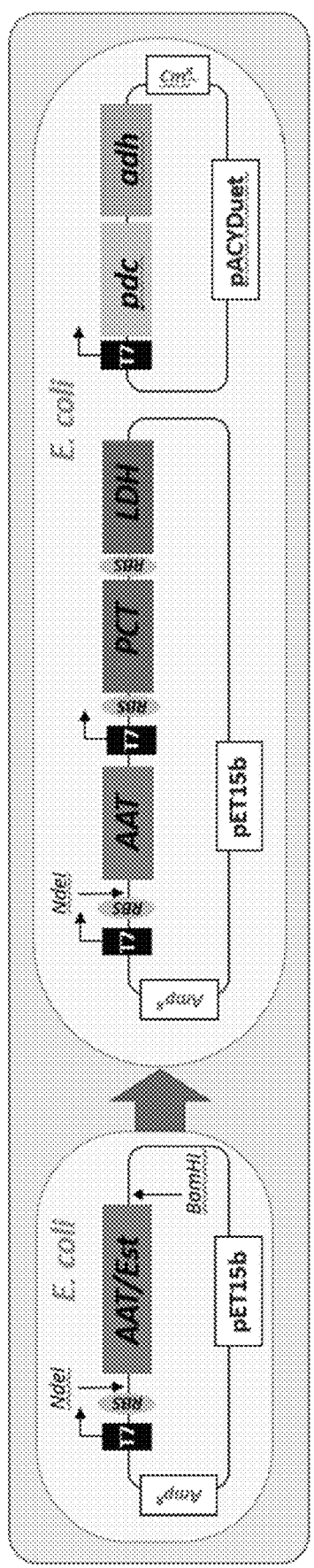
FIG. 4 is graphic showing an example plasmid design for engineering of *E. coli* cells.

FIG. 4 discloses plasmid design for engineering of *E. coli* cells. In an embodiment, *E. coli* cells can be engineered through a two-step cloning process. First, the cells can be cloned with esterase or transferase enzymes using pET15b plasmid at NdeI/BamHI locus in the vector. These plasmids were further cloned with pct/ldh (D/L) operons through CPEC cloning at BamHI locus and co-transformed with pACYDuet plasmid (possessing pdc/adh enzymes).

In an embodiment, codon optimization can be performed for optimization of the process in the expression host. Control of pH and temperature of the reaction can also be performed to maximize the fermentation process and the biocatalysis into fusel lactates. For example, pH may vary in the range of 5 to 10, 6 to 8, or 6.5 to 7.5. For example, temperature may range from 15 to 100° C., such as, for example 22 to 37° C., or 25 to 32° C.

In an embodiment, after the reaction progresses, the fusel lactate can be separated from the remainder of the hydrolyzed biomass by standard liquid extraction and distillation procedures. Using the biosynthesis process disclosed herein directly from a hydrolyzed biomass can eliminate the cost of glucose and fermenting process additives in the making of the fusel lactates.

In an embodiment, ethyl lactate is produced by the biosynthesis, and a transamination reaction is then performed to synthesize lactates with other alkyl groups.

Applications for Fusel Lactates

Fusel lactates disclosed herein can be used in various industries such as: fragrance in perfumes, flavoring agents in food, and solvents in a variety of industries ranging from pharmaceuticals and cleaning products to coatings and adhesives. The main environmental draw of fusel lactates, particularly ethyl lactate, comes from their potential to replace hazardous industrial solvents such as toluene (pharmaceuticals) and xylene (printing, rubber, paint, leather). Xylene and toluene are both carcinogenic and hazardous to the environment, whereas ethyl lactate is noncarcinogenic, completely biodegradable, and approved by the FDA for use in food. A further benefit of ethyl lactate is its low vapor pressure at 25° C. (3.75 mm Hg) when compared to xylene and toluene (8.84 and 28.4 mm Hg, respectively). See PubChem, Compound Summary for Toluene, Benzene, Ethyl Lactate. National Institute of Health, U.S. National Library of Medicine, National Center for Biotechnology Information. Accessed Mar./3/2019. That lower vapor pressure limits the amount of solvent to which workers are exposed and that is emitted to the environment, making for safer workplaces and minimizing environmental impact. Ethyl lactate as disclosed herein, is in accordance with several principles of green chemistry, these are: it can be produced from renewable resources; it is completely biodegradable; it does not deplete ozone; it is non-corrosive; and it can be produced using hybrid technologies requiring less capital and energy.

In an embodiment, the fusel lactate compound is used in autoignition engines or spark ignition engines. They can be used as additives (e.g., 0.1 to 30%, 1 to 20%, or 3 to 10% by volume) in blends with conventional fuels such as diesel, biodiesel, gasoline, other biofuels, Fischer-Tropsch, or marine fuels. In an embodiment, a 10%, 20%, or 30% blend of the fusel lactate with Eli) fuel can be used. In an embodiment, the fusel lactate can be used up to 85% of the fuel composition (similar to E85 fuel). These engines and conventional fuels are known in the art, and do need description in detail to those of ordinary skill in the art.

A section including working examples follows, but, as with the rest of the detailed description, should not be read to be limiting on the scope of the claims.

Examples

This work involved two separate sets of examples (Generally, Example Set 1 and Example Set 2). Example Set 1 set was performed to determine the optimum temperature and pH conditions for each enzyme to catalyze the pNPA reaction. Three temperatures (22, 30, 37° C.) and three pH conditions (pH of 6, 7, 8) were tested. The temperature and pH condition which led to the highest product concentration were selected as the conditions to be used for each enzyme in Example set 2. The second set of examples was a kinetics reaction assay where reaction progress was measured at five time points (0, 15, 30, 60, 120) for six different initial pNPA concentrations (0, 25, 50, 100, 150, 200 µM).

Procedures common to both sets of examples included: culturing and collection of cloned cells; lysing of cloned cells, and methodology for measuring protein concentration.

Details of these common methods are provided for both sets of Examples immediately below.

Cell Culturing Protocol:

Inoculation of a LB broth (5 to 50 ml) from glycerol stock of *E. coli* bacteria was performed. An antibiotic (carbenicillin at 100 µg/ml) was used to selectively culture correct bacteria and ensure retention of enzyme.

A glycerol stock of BL21 type for a control and each of the enzymes being studied in this work was used to inoculate 5 ml of lysogeny broth in test tubes. These tubes were kept in 37° C. incubators and agitated at 230 RPM. Two hours post inoculation, each culture was induced with Isopropyl β-d-1-thiogalactopyranoside in concentration of 1 mM and returned to the incubator at the same conditions as before induction.

After a total incubation period of 24 hours, the cells were pelleted down, supernatant was removed, and the cells were stored at −80° C. for another 24-hour period. Then cells were lysed using SoluLyse solution.

Cell Lysing Protocol:

After cells had been stored at −80° C. for 24 hours (with the exception of the enzyme kinetics experiment for which cells were stored for 7 days), they were lysed with SoluLyse. SoluLyse was added in a ratio of 100 µl per ml of culture pelleted down. The pellet was gently mixed into the SoluLyse using a pipette.

The SoluLyse cell mixture was then incubated at room temperature (∼23° C.) with slight agitation for 20 minutes. At this point, lysing was complete. The mixture of soluble and insoluble proteins was used as the cell lysate added to the reaction.

Determination of Enzyme Concentration

To determine the concentration of protein in the cell lysate, Bradford's reagent was used. For this process, 200 µl of Bradford's reagent were added to 20 µl of 20 times diluted lysate and incubated in a plate reader and allowed to bind in the absence of light for 5 minutes with agitation. This was done in a 96-well plate. After 5 minutes, the absorbance of the protein dye mixture was taken at a wavelength of 595 nm. A standard curve based on porcine esterase was used to convert from absorbance at 595 nm to protein concentration. The assumption was made that the porcine esterase curve would be reflective of the protein concentration for the enzymes studied in this work.

Example Set 1: Temperature and pH

Example Set 1 had the objective of determining the optimum temperature and pH conditions at which to run experiments for enzymatic activity characterization. As such, temperature and pH were the only conditions that varied in this experiment. Both were tested at three different levels which were similar to normal cell conditions: 22, 30 and 37° C. for temperature and 6, 7, and 8 for pH. This resulted in a total of 9 different combinations of conditions, seen in Table 2:

TABLE 2

|  | 25° C. | 30° C. | 37° C. |
| --- | --- | --- | --- |
| pH 6 | pH 6; 25° C. | pH 6; 30° C. | pH 6; 37° C. |
| pH 7 | pH 7; 25° C. | pH 7; 30° C. | pH 7; 37° C. |
| pH 8 | pH 8; 25° C. | pH 8; 30° C. | pH 8; 37° C. |

These were tested for all 8 enzymes from Table 1, as well as the wild type control, and a blank containing no enzyme. All of the runs contained protein, pNPA, and phosphate buffer as seen in Table 3:

TABLE 3

| Component | Amount | Conc. Added | Conc. Final |
| --- | --- | --- | --- |
| Protein | 100 µl | 250 µg/ml | 50 µg/ml |
| pNPA | 5 µl | 10 mM | 100 µM |
| P Buffer | 395 µl | 100 mM | 79 mM |
| VReaction | 500 µl | — | — |

The phosphate buffer was of 6, 7, or 8 pH, respectively. Lysate for each enzyme was diluted down to 250 µg/ml to facilitate ease of addition—each blank received an extra 100 µl of phosphate buffer instead of diluted cell lysate. The enzymatic component was added last and was the catalyst to initialize the reaction. The reactions were performed in three deep 96-well plates each of which was incubated at one of the temperature conditions. Agitation was provided by incubators shaking at 230 RPM.

Readings were made at 30 and 60 minutes following the initialization of the reaction. To make a reading, 200 µl of the reaction volume were transferred from the deep well plates to standard 96-well plates. The pNP product of the pNPA reaction assays is detected through Absorbance at a wavelength of 410 nm.

Figure 5:
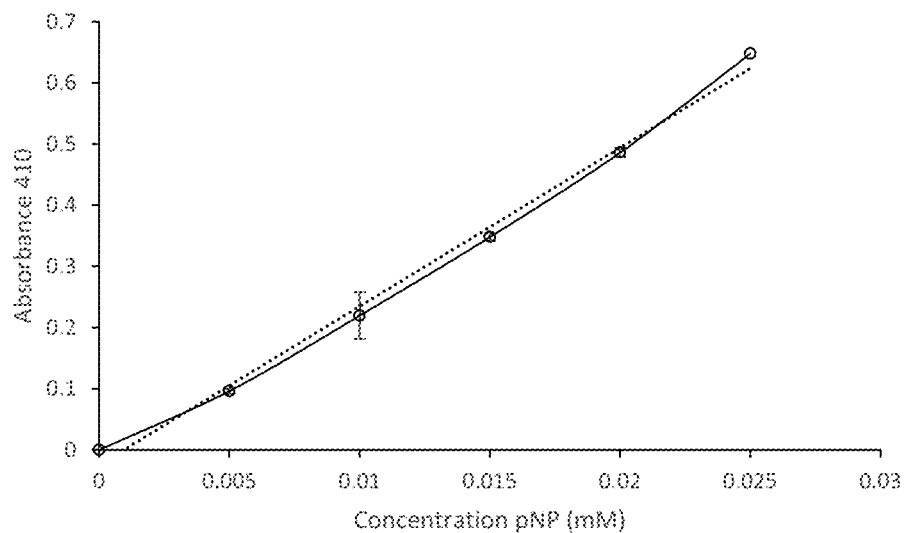
FIG. 5 is plot of the absorbance of pNP as a standard (dotted line) vs. the observed data (solid line).

A curve was generated to convert from absorbances to pNP concentration. The relationship between a colored chemical and its absorbance is usually linear and can be used to convert absorbance values into chemical concentrations. To know how much pNP was being detected through absorbance, it was necessary to create a standard curve to obtain values for the relationship between the concentration of pNP and the absorbance of pNP. Creating a standard curve involved creating samples of different pNP concentrations. For the pNP to give color, it needed to be ionized. Accordingly, pNP was ionized in the presence of NaOH at a concentration of 0.4 g/ml. A standard curve was created by taking the absorbance of pNP at various known concentrations. FIG. 5 shows the standard curve for pNP (dotted line). As also seen in FIG. 5, the data (solid line) closely follows a linear pattern over the concentration range being tested for pNP. The $R2$ value for the linear regression is 0.9939. The formula for converting from absorbance to pNP, derived from that linear regression, is seen in Equation A1:

$$[pNP]=(Abs+0.0244)/25.929 \quad [A1]$$

This equation was used throughout the experiment to convert absorbance values into pNP concentrations.

For Example Set 1, plots showing the final pNP concentration for each enzyme, temperature, and pH concentration are shown. Table 5 shows the conditions that resulted in the highest and second highest conversion of pNPA to pNP for each enzyme.

TABLE 4

| Parameter | AcAlt | | AXE2 | | tEstA | | EstA | | EOA | | CE | | EEB1 | | DAG | | PET | |
|---|---|---|---|---|---|---|---|---|---|---|---|---|---|---|---|---|---|---|
| | °C. | pH | °C. | pH | °C. | pH | °C. | pH | °C. | pH | °C. | pH | °C. | pH | °C. | pH | °C. | pH |
| Highest | 30 | 8 | 37 | 6 | 30 | 8 | 22 | 7 | 30 | 7 | 37 | 8 | 22 | 7 | 30 | 8 | 37 | 8 |
| 2nd Highest | 22 | 7 | 30 | 8 | 22 | 7 | 37 | 8 | 37 | 7 | 22 | 7 | 30 | 8 | 30 | 6 | 30 | 8 |

As seen in Table 4, there was no one overall condition that was best for all of the enzymes. There was at least one enzyme that performed best at each of the three temperatures and at each of the three pH conditions. With the exception of AXE2 and EEB1, all performed sufficiently well at all conditions.

Figure 6:
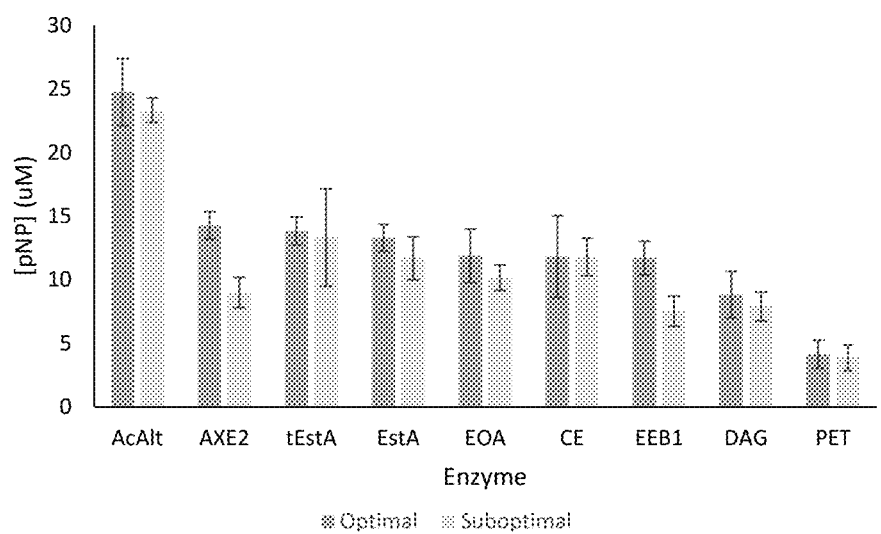
FIG. 6 is a graph showing the best and second best pNP concentrations attained for each of the studied enzymes.

FIG. 6 graphically represents the optimal (best) and suboptimal (second best) pNP concentrations attained for each of the studied enzymes. As shown in FIG. 6, the best performing enzyme was from AcAlt. All of the enzymes performed better than the PET control. Most of the suboptimal conditions had performed within the error of the optimal conditions, with the exception of AXE2 and EEB 1.

Example Set 2

In Example Set 2, a kinetics reaction assay was performed on the enzymes from Table 1. This experiment had the objective of determining which of the enzymes in this study exhibits the highest esterase activity. That enzymatic activity was tested for at the ideal temperature and pH conditions determined in the optimization experiment.

One deviation from the common protocols for Example Set 2 was that cell pellets had been stored in −80° C. for seven days instead of the usual 24 hours. In addition, the lysing process included more vigorous agitation.

To determine the kinetic activity for each enzyme, substrate concentration was varied and measured at different time points. In addition to testing each enzyme, a wild type *E. coli* PET control (see Table 1) was run at its optimal conditions. A blank containing pNPA but no enzyme was also included for each of the temperature pH combinations to be tested.

Initial pNPA concentrations were tested at 0, 25, 50, 100, 150, 200 µM. Measurements were made at 0, 15, 30, 60, and 120 minutes. The reaction conditions which remained constant throughout all the reactions were as seen in Table 5:

TABLE 5

| Component | Amount | Conc. Added | Conc. Final |
|---|---|---|---|
| Protein | 200 µl | 250 µg/ml | 50 µg/ml |
| pNPA | 20 µl | Varied | Varied |
| P Buffer | 780 µl | 100 mM | 78 mM |
| VReaction | 1000 µl | — | — |

The phosphate buffer was of pH 6, 7, or 8 as determined to be best from Example Set 1. Stock solutions of pNPA were made in different concentrations such that adding 20 µl to the reaction would result in the corresponding final pNPA concentration (either 25, 50, 100, 150, or 200 µM). Cell lysate was diluted to concentrations of 250 µg/m to allow for uniformity in the volume of lysate added to each reaction. Instead of diluted lysate, each blank received an extra 200 µl of phosphate buffer. This component was added last and marked the initiation of the reaction.

As with the temperature and pH optimization experiment, the reactions were performed in three deep 96-well plates—one plate for each temperature condition to be tested. At each time point following initiation, product pNP concentration was measured. Measurements were made by transferring a 200 µl sample from each reaction to a standard 96-well plate. Absorbance of each sample was then made at a wavelength of 410 µl.

As mentioned, the cell pellets were stored in −80° C. for seven days before being lysed for the kinetics experiment, as opposed to the 24 hours of storage before the optimization experiment.

For the Enzyme kinetics experiment, pNP concentration versus time plots, Michaelis-Menten plots, as well as Lineweaver Burk plots are provided. Then plots for $v_{max}$, $k_m$, $k_{cat}$, and the specificity constant are provided, with values summarized in Table 6.

Figure 7:
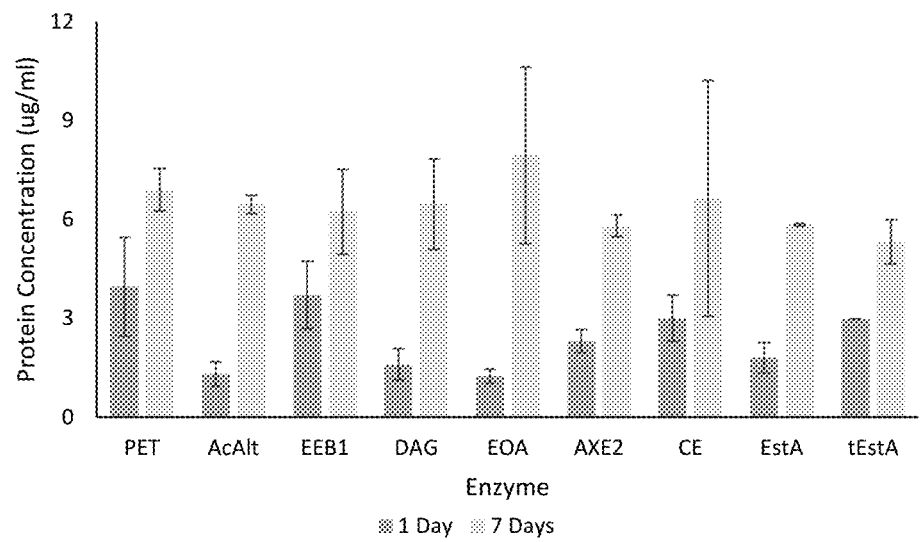
FIG. 7 is a graph showing amount of protein concentrations obtained from lysing pellets that were stored for one day and for seven days before lysing.

The amount of protein concentrations obtained from lysing pellets that were stored for different lengths is shown in FIG. 7. (Pellets were stored at −80° C. for one day and for seven days before lysing.)

The amount of protein recovered from the pellets that were stored for seven days was always greater than the amount of protein recovered from pellets stored for 24 hours. In some cases, such as EEB1, the increase was roughly 50%, and in other cases such as EOA, the increase was 500%. The data shows a correlation between time stored and amount of protein obtained from cell lysate.

Once lysing was complete, the optimal conditions shown in Table 4 were used to perform the enzyme kinetics experiment. Data collected from the kinetics experiment was plotted to form Michaelis-Menten plots. See FIG. 8, which shows data from the control and the alcohol acyltransferase enzymes, and FIG. 9, which shows data from the control and esterase enzymes.

Figure 8:
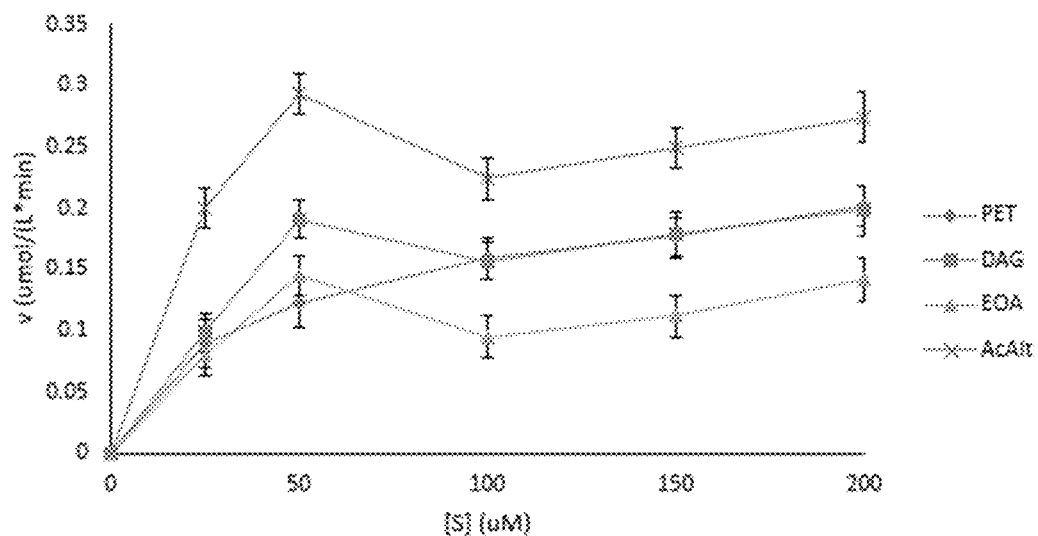
FIG. 8 is a Michaelis-Menten graph showing kinetic reaction data from a control and from alcohol acyltransferase enzymes.
Figure 9:
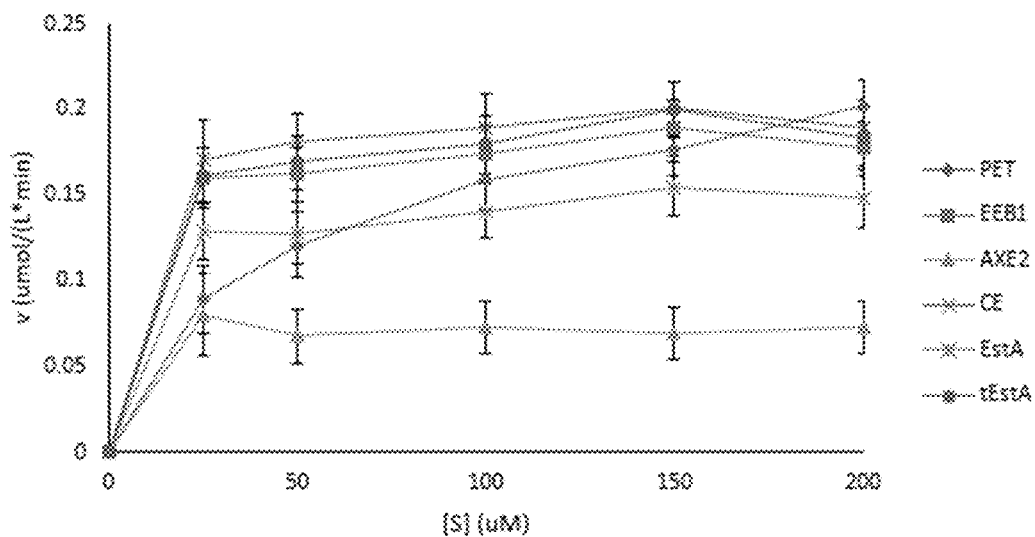
FIG. 9 is a Michaelis-Menten graph showing kinetic reaction data from a control and from esterase enzymes.

Both FIG. 8 and FIG. 9 show a general logarithmic trend, and level out near an initial pNPA concentration of 100 µM. The alcohol acyltransferase enzymes all showed better conversion at a pNPA concentration of 50 µM before going lower at a pNPA concentration of 100 µM.

Figure 10:
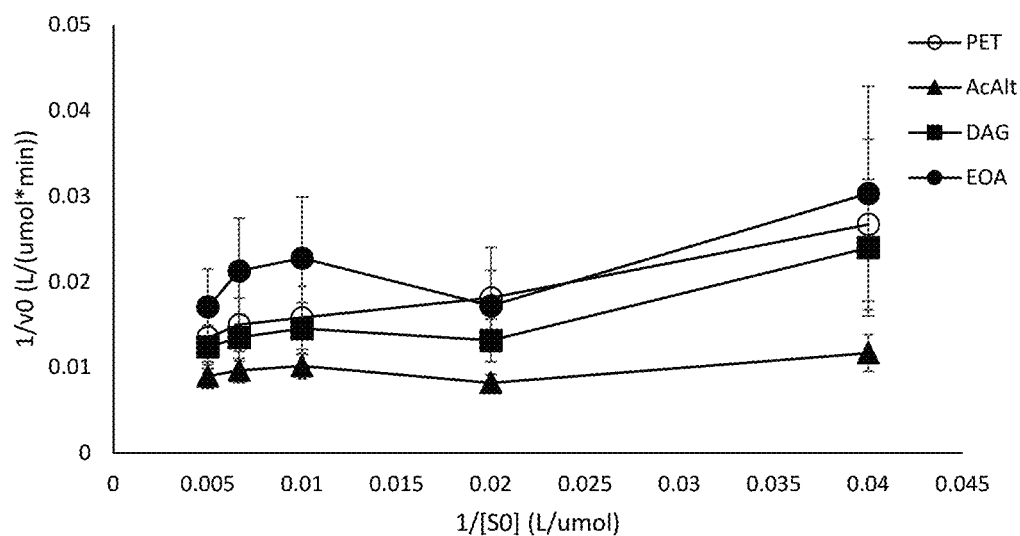
FIG. 10 is a Lineweaver-Burke plot showing data collected from enzyme kinetics experiment for alcohol acyl transferase enzymes.
Figure 11:
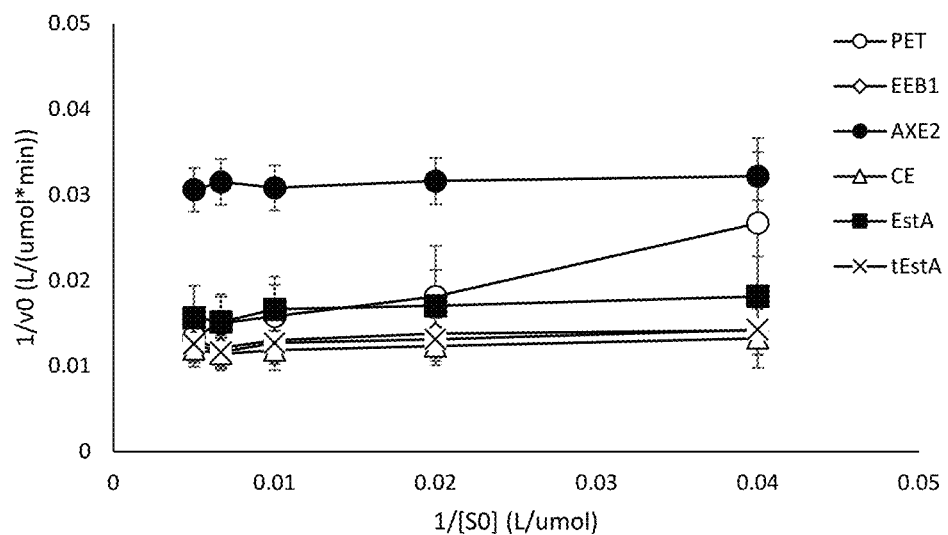
FIG. 11 is a Lineweaver-Burke plot showing data collected from enzyme kinetics experiment for esterase enzymes.

FIG. 10 (alcohol acyl transferase enzymes) and FIG. 11 (esterase enzymes) show the Lineweaver-Burk plots put together from the data collected in the enzyme kinetics experiment. Ideally, data on this type of plot forms a linear line. Some data was close to linear—such as the control PET and EstA— while other data was far from linear such as EOA and AcAlt.

Further Michaelis-Menten analysis was performed by deriving slope and y-intercept values derived from linear regressions used to fit the data. These were used to calculate the theoretical $v_{max}$ values for the enzymes, which are shown in FIG. 12.

Figure 12:
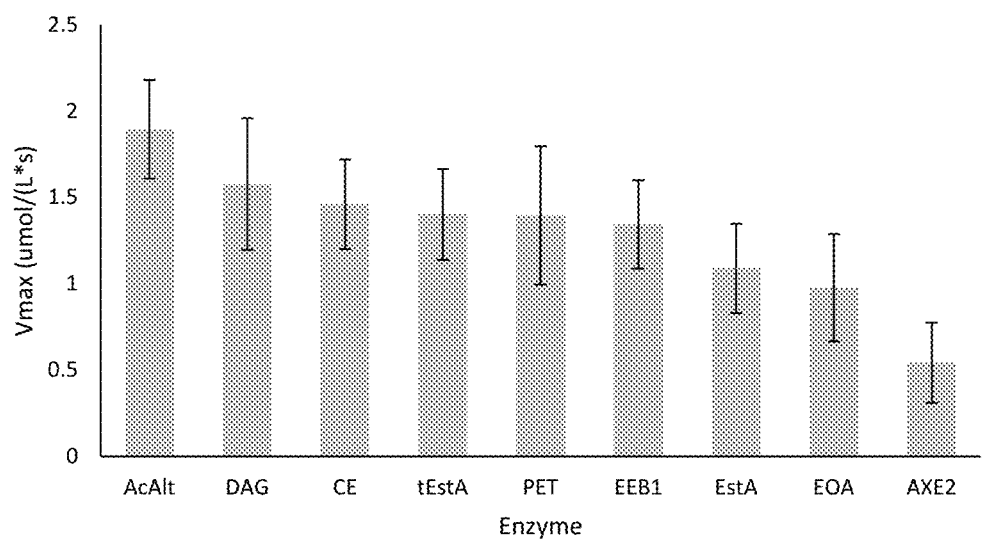
FIG. 12 is a graph showing the $v_{max}$ (highest reaction rate which can be achieved through use of that enzyme as a biocatalyst) for the example enzymes.

The $v_{max}$ represents the highest reaction rate which can be achieved through use of that enzyme as a biocatalyst for a given reaction, and these values are given in FIG. 12 for each enzyme for their ability to convert pNPA to pNP. Alcohol acyltransferase enzymes, AcAlt and DAG, had the highest maximum reaction velocities, while an esterase, AXE2, had the lowest. The control had a maximum reaction rate better than half of the enzymes.

Figure 13:
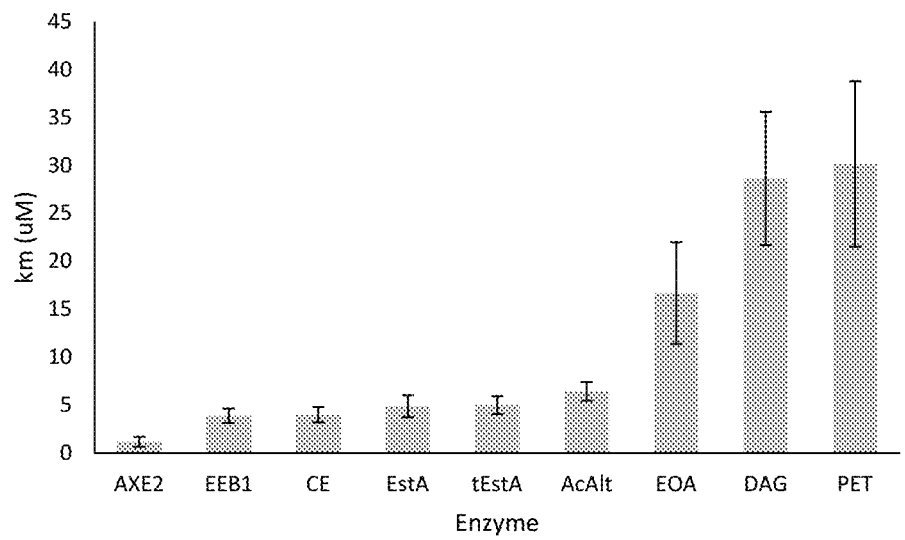
FIG. 13 is a graph showing the $k_m$, or Michaelis-Menten constant of the example enzymes.

Next, another kinetic parameter, $k_m$, was calculated. Results for the Michaelis-Menten model are shown in FIG. 13. The $k_m$, or Michaelis-Menten constant, represents the amount of substrate that is required for the enzyme to operate at one half of the theoretical maximum reaction velocity. Unlike the $v_{max}$ value, a lower $k_m$ value is desired. In this light, as seen in FIG. 13, the five esterase enzymes all out-performed the three alcohol acyl transferase enzymes. All of the enzymes in the study out-performed the control.

Figure 14:
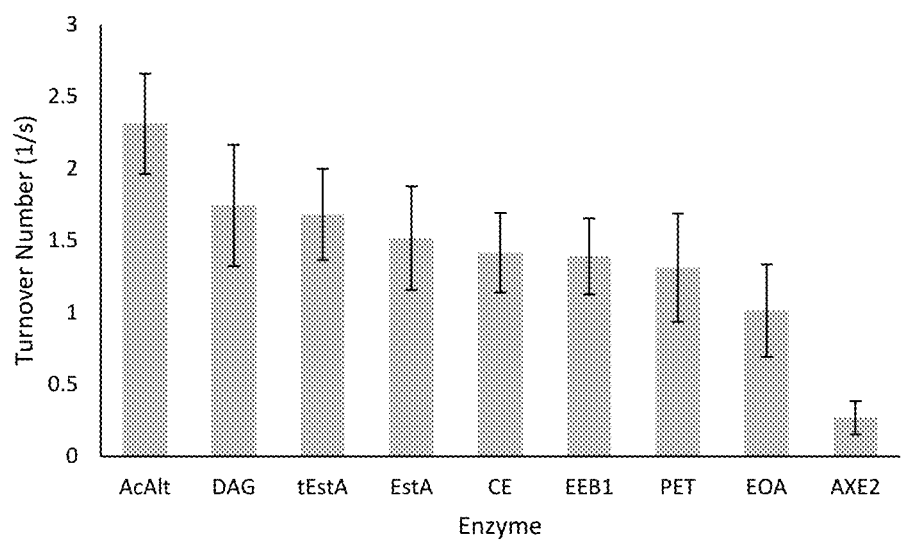
FIG. 14 is a graph showing the $k_{cat}$ turnover number constant of the example enzymes.

At this point, $k_{cat}$, the turnover number, was calculated. The turnover number is a representation of how many molecules are being processed by each enzyme per unit of time. For these calculations, it was assumed that all of the enzymes detected through the use of Bradford's reagent were the desired enzyme. Calculated values for the turnover number are seen in FIG. 14. It should be noted that the assumption that all of the enzymes detected by the Bradford's reagent are composed of the enzymes in this study lowers the value of the turnover number. However, as the assumption is made for all of the enzymes, it is fair for comparison purposes. As seen in FIG. 14, AcAlt and DAG were the enzymes with the highest turnover number. The lowest performing enzymes in this kinetic parameter were EOA and AXE2, both of which had lower turnover numbers than the control.

Figure 15:
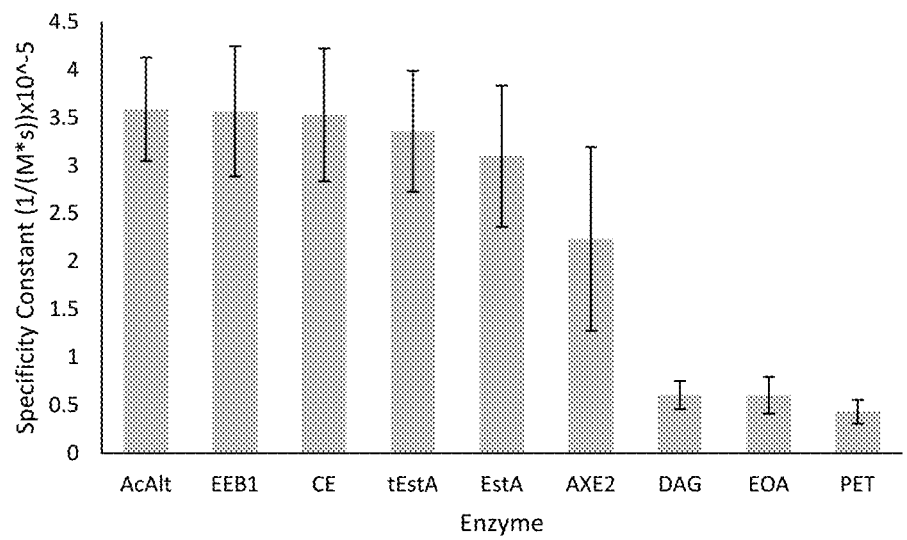
FIG. 15 is a graph showing the specificity constant of the example enzymes.

Following the analysis for the turnover number, the specificity constant was calculated from the Michaelis Menten model, with results seen in FIG. 15. The values of the specificity constant are for use in comparing the performance of the enzymes. All of the enzymes out-performed the PET control, with DAG and EOA having much lower specificity constants than the other enzymes. AcAlt, EEB1, CE, tEstA, and EstA were the top performing enzymes, and their average values were all within the standard error of the others.

A summary of the values reported for the kinetic parameters seen in FIGS. 12, 13, 14, and 15 are shown in Table 6:

TABLE 6

| | $v_{max} \times 10^{-6}$ (molL$^{-1}$s$^{-1}$) | $k_m \times 10^{-6}$ (M) | kcat (s$^{-1}$) | $k_{cat}/k_m \times 10^5$ (Lmol$^{-1}$s$^{-1}$) |
| --- | --- | --- | --- | --- |
| AcAlt | 1.89 ± 0.29 | 6.44 ± 0.97 | 2.31 ± 0.35 | 3.59 ± 0.54 |
| EEBI | 1.34 ± 0.26 | 3.90 ± 0.74 | 1.39 ± 0.26 | 3.56 ± 0.68 |
| CE | 1.46 ± 0.33 | 4.01 ± 0.76 | 1.42 ± 0.28 | 3.53 ± 0.69 |
| tEstA | 1.40 ± 0.29 | 5.01 ± 0.94 | 1.68 ± 0.32 | 3.36 ± 0.63 |
| EstA | 1.09 ± 0.05 | 4.89 ± 1.16 | 1.52 ± 0.36 | 3.10 ± 0.74 |
| AXE2 | 0.54 ± 0.25 | 1.20 ± 0.51 | 0.27 ± 0.12 | 2.23 ± 0.96 |
| DAG | 1.58 ± 0.38 | 28.6 ± 6.94 | 1.74 ± 0.42 | 0.61 ± 0.15 |
| EOA | 0.98 ± 0.31 | 16.7 ± 5.30 | 1.01 ± 0.32 | 0.61 ± 0.19 |
| PET | 1.40 ± 0.40 | 30.1 ± 8.62 | 1.31 ± 0.38 | 0.44 ± 0.12 |

The kinetic parameter data seen in Table 6 shows that different combinations of Michaelis-Menten constants and turnover numbers can give similar specificity constants. Even though the enzymes tested did not out-perform the control PET in every category, overall, PET had the worst performance.

Example Set 3 In Vivo Examples

E. coli cells were engineered through two step cloning. First, the cells (E. coli BL21-DE3, a commercially available genetic transformation-ready strain) were cloned with esterase or transferase enzymes using pET15b plasmid at NdeI/BamHI locus in the vector. These plasmids were further cloned with pct/ldh (D/L) operons through CPEC cloning at BamHI locus and co-transformed with pACY-Duet plasmid (possessing pdc/adh enzymes).

Specifically, plasmids were constructed (PT7::RBS:Gene*::PT7::RBS:pct::RBS:ldh in pET15b) and cloned in E. coli BL21-DE3 with ethanol producing plasmid (pACY-Duet-Zm-pdc-Zm-adh). See FIG. 4. Cells were cultivated with high-cell density in M9 medium and induced with 1 mM IPTG.

Figure 16:
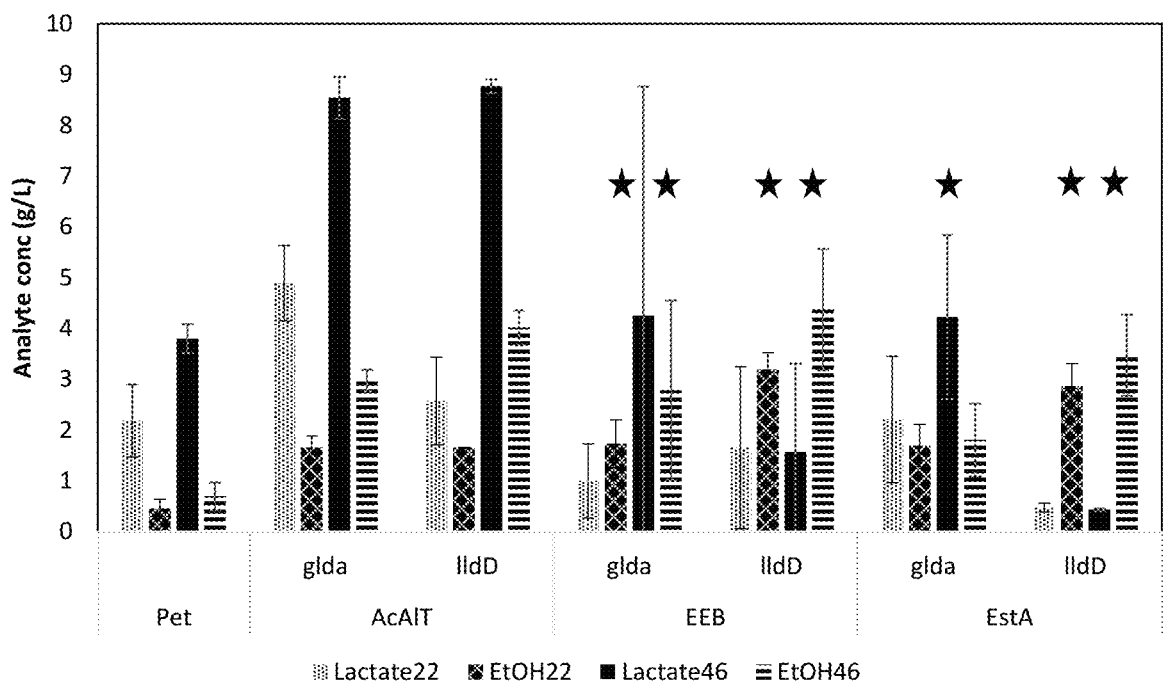
FIG. 16 is a graph showing HPLC analysis of alcohol acyl transferase enzyme supernatants (collected after 22 h and 46 h of incubation).
Figure 17:
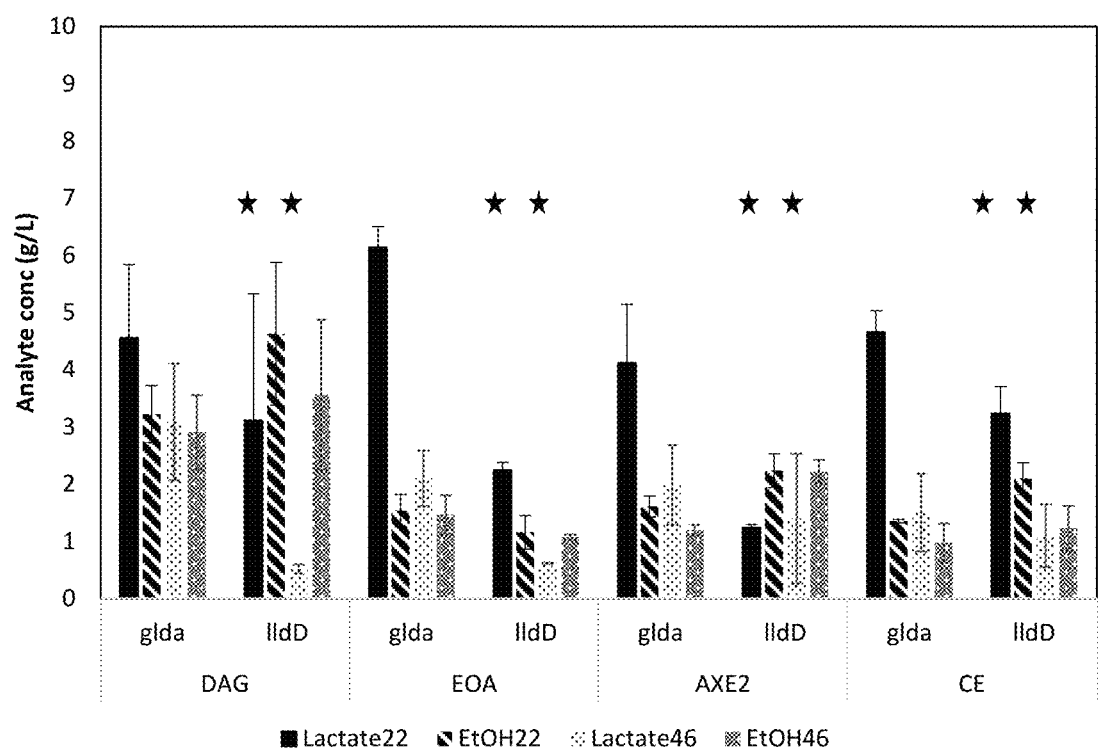
FIG. 17 is a graph showing HPLC analysis of esterase enzyme supernatants (collected after 22 h and 46 h of incubation).

Culture supernatants were analyzed through HPLC (for ethanol and lactate) and GC-MS (for esters). Esterase-A yielded highest ethyl lactate (3.5±1.5 mg/L) and ethyl acetate (16±8 mg/L). FIGS. 16 and 17 show the HPLC analysis of culture supernatants (collected after 22 h and 46 h of incubation) of mutants with the genes (using pET15b possessing cells as the control) cultivated with high-density in hybrid M9 medium (without any external supplementation of ethanol or lactic acid/s) displayed differential concentrations of (D/L) lactate and ethanol.

Figure 18:
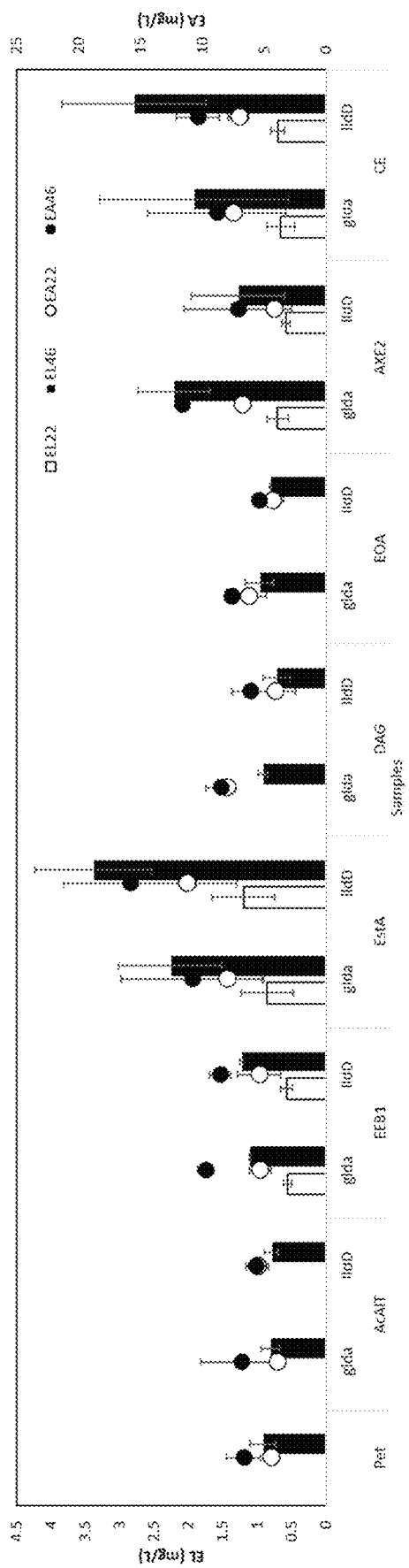
FIG. 18 is a GC-MS analysis of a first set of culture supernatants (collected after 22 h and 46 h of incubation) of mutants extracted with chloroform.
Figure 19:
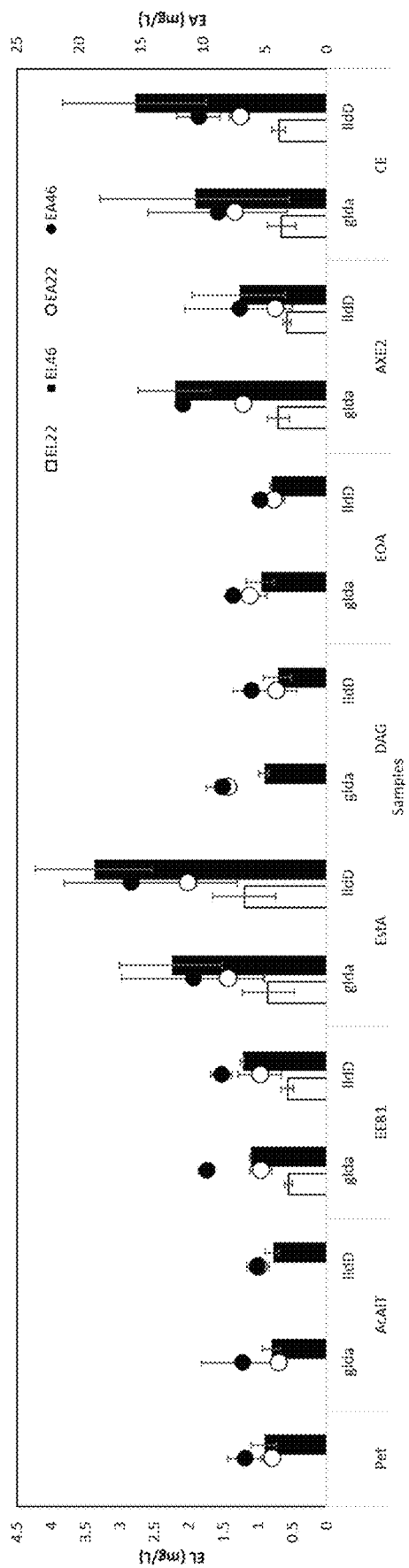
FIG. 19 is a GC-MS analysis of a second set of culture supernatants (collected after 22 h and 46 h of incubation) of mutants extracted with chloroform.

FIGS. 18 and 19 show a GC-MS analysis of culture supernatants (collected after 22 h and 46 h of incubation) of mutants extracted with chloroform. These exhibited significant ethyl lactate and ethyl acetate production in case of esterases (EEB1, EstA, AXE2 and CE).

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. Unless the context indicates otherwise, all percentages and averages are by weight. If not specified above, the properties mentioned herein may be determined by applicable ASTM standards, or if an ASTM standard does not exist for the property, the most commonly used standard known by those of skill in the art may be used. The articles "a," "an," and "the," should be interpreted to mean "one or more" unless the context indicates the contrary.

What is claimed is:

1. A process for converting a glucose-containing hydrolyzed biomass into a fusel lactate, the process comprising:
expressing an esterase gene in a bacterial host, the bacterial host being added to or already present in the glucose-containing hydrolyzed biomass;
maintaining conditions suitable for fermenting in the hydrolyzed biomass, the fermenting producing an alcohol and a lactate; and
catalyzing through an enzyme encoded by the esterase gene, a reaction from the alcohol and lactate to form a fusel lactate in the bacterial host;
wherein the enzyme is selected from the group consisting of: ethyl-ester-synthase-1, acetylxylan-esterase-2, carbohydrate-esterase, esterase-A, truncated-esterase-A, and combinations thereof;
wherein the esterase gene is obtained from an organism selected from: *Komagataella phaffii, Saccharomyces cerevisiae, Brettanomyces bruxellensis,* or *Pseudomonas aeruginosa*.

2. The process of claim 1, wherein the fusel lactate is selected from the group consisting of: ethyl lactate, isopentyl lactate, isopropyl lactate, (iso)butyl lactate, and (iso)pentyl lactate.

3. The process of claim 1, wherein the bacterial host produces a fermentation strain that produces alcohol.

4. The process of claim 1, wherein the reaction is further catalyzed by organic acids, Coenzyme A, adducts thereof, or combinations thereof also present in the hydrolyzed biomass.

5. The process of claim 1, wherein the esterase gene is selected from EEB1, CE, tEstA, and EstA or combinations thereof.

6. The process of claim 1, wherein the maintaining conditions suitable for fermenting include maintaining a pH of 6 to 8, and a temperature of 22 to 37° C.

7. The process of claim 1, wherein the bacterial host is cloned with esterase enzymes using a pET15b plasmid at an NdeI/BamHI locus of the bacterial host.

8. The process of claim 1, further comprising separating the fusel lactate from a remainder of the hydrolyzed biomass by extracting it and distilling it from the hydrolyzed biomass.

9. The process of claim 1, wherein the bacterial host is *Corynebacterium glutamicum*.

10. The process of claim 1, wherein the enzyme has a $k_m$ for producing ethyl lactate;
and the $k_m$ is less than $30.2\times10^{-6}$M.

11. A process for converting a glucose-containing hydrolyzed biomass into a fusel lactate, the process comprising:
expressing an esterase gene in a bacterial host, the bacterial host being added to or already present in the glucose-containing hydrolyzed biomass;
maintaining conditions suitable for fermenting in the hydrolyzed biomass, the fermenting producing an alcohol and a lactate; and
catalyzing through an enzyme encoded by the esterase gene, a reaction from the alcohol and lactate to form a fusel lactate in the bacterial host;
wherein the esterase gene is selected from EEB1, CE, tEstA, and EstA or combinations thereof;
wherein the enzyme has a $k_m$ and a $v_{max}$ for producing ethyl lactate, and the $k_m$ is less than $30.2\times10^{-6}$M and the $v_{max}$ is from $1.5\times10^{-6}$ mol/(L*s) to $2\times10^{-6}$ mol/(L*s).

12. The process of claim 11, wherein the bacterial host is cloned with esterase enzymes using a pET15b plasmid at an NdeI/BamHI locus of the bacterial host.

13. The process of claim 12, wherein the esterase gene is selected from EEB1, CE, tEstA, and EstA or combinations thereof.

14. The process of claim 1, wherein the bacterial host is *E. Coli*.

15. The process of claim 11, wherein the esterase gene is obtained from an organism selected from: *Komagataella phaffii, Brettanomyces bruxellensis,* or *Pseudomonas aeruginosa*.

16. A process for converting a glucose-containing hydrolyzed biomass into a fusel lactate, the process comprising:
expressing an acyl-alcohol transferase gene, esterase gene, or both in a bacterial host, the bacterial host being added to or already present in the glucose-containing hydrolyzed biomass;
maintaining conditions suitable for fermenting in the hydrolyzed biomass, the fermenting producing an alcohol and a lactate; and
catalyzing through an enzyme encoded by the acyl-alcohol transferase gene or -esterase gene, a reaction from the alcohol and lactate to form a fusel lactate in the bacterial host;
wherein the enzyme is selected from the group consisting of: ethyl-ester-synthase-1, acetylxylan-esterase-2, carbohydrate-esterase, esterase-A, truncated-esterase-A, diacylglycerol-transferase, ethanol-o-acyltransferase, propionate CoA transferase, and combinations thereof;
wherein the acyl-alcohol transferase gene or esterase gene are obtained from an organism selected from: *Komagataella phaffii, Saccharomyces cerevisiae, Brettanomyces bruxellensis,* or *Pseudomonas aeruginosa*.

17. The process of claim 11, wherein the fusel lactate is ethyl lactate, and the the esterase gene is selected from EEB1 and CE.

18. The process of claim 16, wherein the bacterial host is cloned with esterase enzymes using a pET15b plasmid at an NdeI/BamHI locus of the bacterial host.

19. The process of claim 16, wherein the enzyme has a $k_m$ for producing ethyl lactate and the $k_m$ is less than $30.2\times10^{-6}$ M.

20. The process of claim 16, wherein the enzyme is selected from the group consisting of: diacylglycerol-transferase, ethanol-o-acyltransferase, propionate CoA transferase, and combinations thereof.

* * * * *